United States Patent
Cuschieri et al.

(10) Patent No.: US 6,730,061 B1
(45) Date of Patent: May 4, 2004

(54) MULTIPLE HYPODERMIC NEEDLE ARRANGEMENT

(76) Inventors: Alfred Cuschieri, Stratkiness Low Rd., St. Andrews Fife KY16 9TY (GB); Timothy G. Frank, 37 Naughton Road, Wormit Newport-On-Tay Fife DD68NG (GB); Wei Xu, 39 Owlbeech Place, Horsham, RH13 6PQ (GB)

( * ) Notice: Subject to any disclaimer, the term of this patent is extended or adjusted under 35 U.S.C. 154(b) by 0 days.

(21) Appl. No.: 09/497,289

(22) Filed: Feb. 3, 2000

(51) Int. Cl.[7] .............................................. A61M 5/178
(52) U.S. Cl. .................. 604/158; 604/159; 604/164.09; 604/164.01; 604/264; 604/272
(58) Field of Search ................. 604/158, 159, 604/163, 164.01, 164.06, 164.09, 164.12, 170.03, 173, 264, 272, 515, 154, 530, 531; 606/108, 144, 186, 27, 28, 29, 32, 167, 185

(56) References Cited

U.S. PATENT DOCUMENTS

| | | | | |
|---|---|---|---|---|
| 4,511,356 A | * | 4/1985 | Froning et al. | 604/170.01 |
| 5,026,350 A | * | 6/1991 | Tanaka et al. | 604/158 |
| 5,354,279 A | * | 10/1994 | Hofling | 604/164.12 |
| 5,419,777 A | * | 5/1995 | Hofling | 604/264 |
| 5,472,441 A | * | 12/1995 | Edwards et al. | 606/41 |
| 5,628,734 A | * | 5/1997 | Hatfalvi | 604/272 |
| 5,722,981 A | * | 3/1998 | Stevens | 606/144 |
| 6,056,744 A | * | 5/2000 | Edwards | 606/41 |
| 6,425,887 B1 | * | 7/2002 | McGuckin et al. | 604/272 |
| 6,428,634 B1 | * | 8/2002 | Besselink et al. | 148/402 |
| 6,432,092 B2 | * | 8/2002 | Miller | 604/164.12 |

FOREIGN PATENT DOCUMENTS

| | | |
|---|---|---|
| GB | 2 124 503 A | 1/1986 |
| GB | 2 269 538 A | 10/1996 |

* cited by examiner

*Primary Examiner*—Tuan N. Nguyen
(74) *Attorney, Agent, or Firm*—St. Onge Steward Johnston & Reens LLC

(57) ABSTRACT

A hypodermic needle is provided comprising a first, hollow needle having movably secured therein one or more further, hollow needles. Each further needle and part of the hypodermic needle being movable relative to one another between a stressed position and an unstressed position. In the stressed position, each further needle is substantially parallel to the first needle. In the unstressed position, the free end of each further needle lies beyond the axial and/or radial terminus of the first needle.

12 Claims, 2 Drawing Sheets

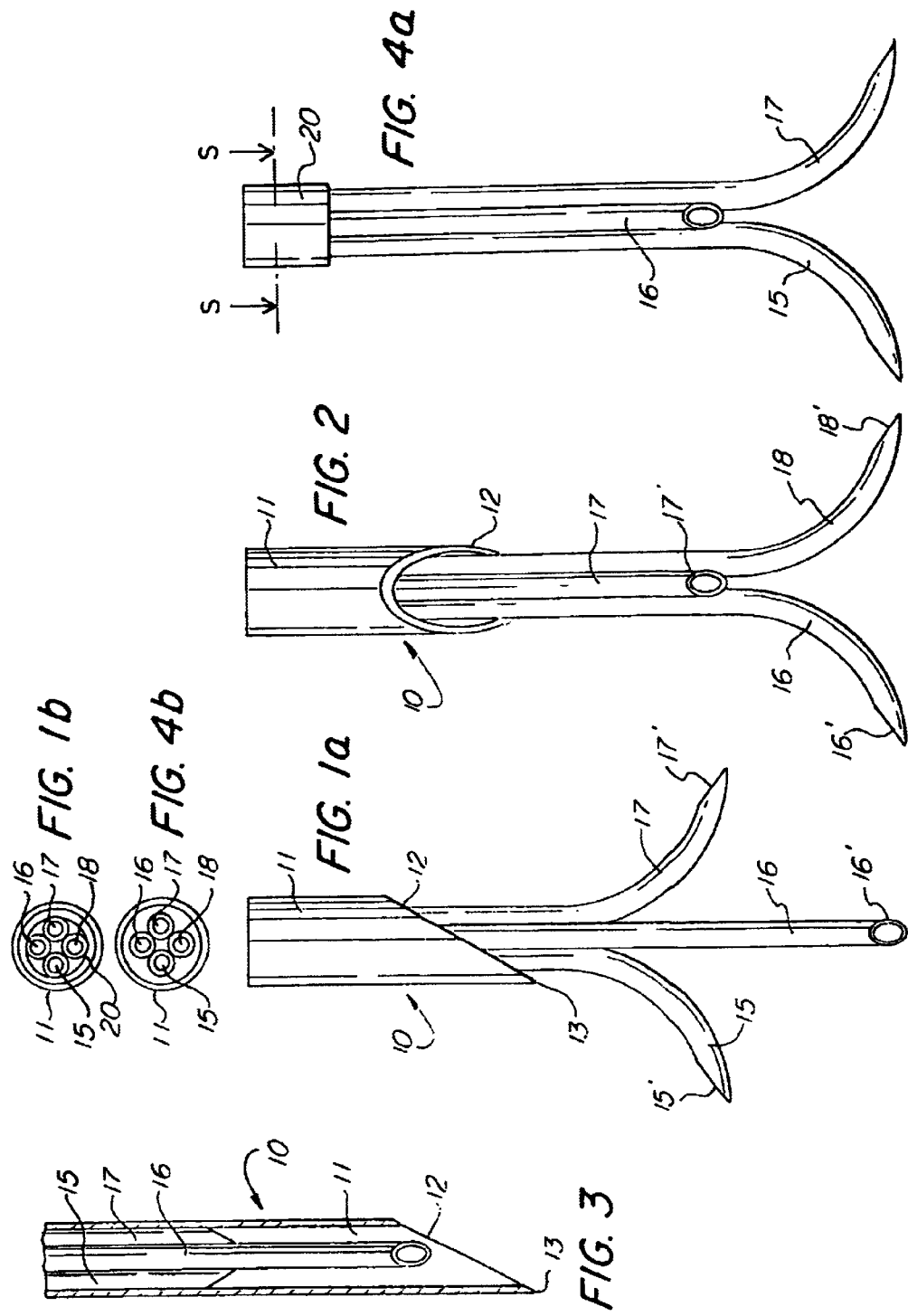

MULTIPLE HYPODERMIC NEEDLE ARRANGEMENT

This invention relates to a hypodermic needle. There are several medical situations where it is desired to deliver substances by injection to a relatively large volume of tissue. If a substance is delivered by a single point injection, the problems that may arise are (a) the substance cannot spread throughout the volume in sufficient time, (b) too much dilution may occur during the spreading, (c) the distribution of the substance within the volume may be very inhomogeneous, and (d) unwanted spreading to regions away from the target volume may occur. One solution to this problem is to give smaller injections at several sites within the target volume. This approach has at least three disadvantages: (a) multiple needle stab wounds are created, (b) accuracy of placement is limited, and (c) the time for the procedure is increased.

A particular example of these difficulties arises in the treatment of liver cancers. Cancers within the liver can be killed with large doses of alcohol. One surgical approach is to expose the liver using open or laparoscopic surgery and inject the tumour at many sites using the same needle. One severe problem of this approach is that considerable bleeding results from the many stab wounds and, more seriously, this bleeding can carry tumour cells into the peritoneal cavity.

Thus, there is a need for a device capable of delivering substances to a relatively large volume of tissue without incurring the above-noted disadvantages of the prior art.

According to the invention there is provided a hypodermic needle comprising a front, hollow needle having movably secured therein one or more further, hollow needles, each said further needle and part of the hypodermic needle being movable relative to one another between a stressed position of the or each further needle, in which each said further needle is substantially parallel to the first needle, and an unstressed position of the or each further needle, in which the free end of each said further needle lies beyond the axial and/or radial terminus of the first needle. Preferably, in the unstressed position the or each said further needle protrudes beyond both the axial and radial termini of the first needle.

An advantage of this arrangement lies in the ability of the or each further needle to spread outwardly from the first hollow needle, thereby permitting injection into a large volume of tissue from a single puncture wound (in the case of plural, further needles); and/or allowing injection to one or more sites remote from the terminus of the first needle.

The creation of a single wound minimises bleeding; reduces the above-noted risk of transfer of cancer cells; and speeds the operation.

Preferably each said further needle is moveable relative to the remainder of the hypodermic needle and lies within the first needle when occupying its stressed position and protrudes from the first needle when occupying its unstressed position. This is the preferred means for advancing the or each further needle to its unstressed position, although alternative arrangements are possible. For example, instead of advancing the or each further needle from within the first needle, an encircling band may be moveable on a bundle of stressed, further needles to release them to their unstressed condition.

Preferably each said further needle is generally straight when occupying its stressed position and curved when occupying its unstressed position, thereby permitting its free end to project beyond the axial and radial terminus of the first needle when the further needle occupies its unstressed position.

The advantageously allows the further needles to be stored within the first needle eg during the puncturing operation and when the apparatus is being filled or transported.

In particularly preferred embodiments, each said further needle includes a circular arc when occupying its unstressed position. The or each said further needle may also include an arc in the range of curvature of 60°–110°, when occupying its unstressed position. The arc may in alternative embodiments lie outside this range of curvature, or may be of infinitely large radius, ie. one or more of the further needles may optionally include a straight portion. The foregoing features advantageously assist the or each further needle to advance through, eg. tissue without causing collateral damage thereto.

Preferably each said further needle is formed of or from a superelastic shape memory alloy (SMA), in particular a heat treated alloy comprising approximately 56% Ni and 44% Ti by weight. Preferably the cold drawn alloy is heat treated at approximately 500° C. for about 10 minutes whilst secured on a former, thereby conferring the preferred shape on the further needles when occupying the unstressed position. These features permit the ready transition from a substantially straight to a substantially curved configuration on advancement of the further needles from within the first, hollow needle. The superelastic shape memory alloy is particularly suitable for embodiments of a said further needle the ratio of whose unstressed radius of curvature to its diameter lies in the range of 100:1 to 10:1.

An SMA is preferred to spring stainless steel because it has a recoverable strain some tens times greater than steel. Thus for a given curve the SMA tube can have up to ten times the diameter of a steel tube; conversely, for a give tube diameter, SMA can have a curve radius down to a tenth of that for steel. Nonetheless, it may be suitable to use steel or other non-superelastic materials for the further needles, eg. in embodiments in which the needle radius of curvature lies outside the range specified above.

Preferably the lengths of two or more of the further needles differ from one another. This, advantageously, assists in the distribution of the substance to the tissues.

Preferably the free end of the or each said longer, further needle is spaced axially and radially from the free ends of the other said further needles when the further needles occupy their extended positions.

Conveniently, the or each said further needle communicates with the interior of a hollow, elongate tube movably lying within the first said needle, the end of the hollow tube remote from the said terminus of the first needle engaging or including a movable actuator member for advancing and retracting the or each said further needle relative to the first needle. This provides a convenient and simple means of moving the or each further needle between its stressed and unstressed positions.

Preferably the interior of the hollow tube communicates with an adaptor for receiving the nozzle of a hypodermic syringe. The hypodermic needle of the invention may also optionally include a detent for securing the hollow tube in a position corresponding to retraction of the or each further needle. This feature improves the safety of the device, since it permits releasable locking of the further needle(s) in a stressed (inoperative) position.

The invention is also considered to reside in the use of a superelastic shape memory alloy in the manufacture of a hypodermic needle.

There now follows a description of preferred embodiments of the invention, by way of example, with reference being made to the accompanying drawings in which:

FIGS. 1a and 1b are respectively, side elevational and cross-sectional views of a hypodermic needle according to the invention with its further needles in the advanced position;

FIG. 2 is a side elevational view of the FIG. 1a arrangement, rotated through 90° about the longitudinal axis of the needles;

FIG. 3 is a partially sectioned view of the arrangement of FIGS. 1 and 2 with the further needles occupying their retracted positions;

FIG. 4a shows a subcomponent of the arrangement of FIGS. 1 to 3;

FIG. 4b is a cross sectional view of the FIG. 4a subcomponent taken on line 5—5 of FIG. 4.

Figure 5A:
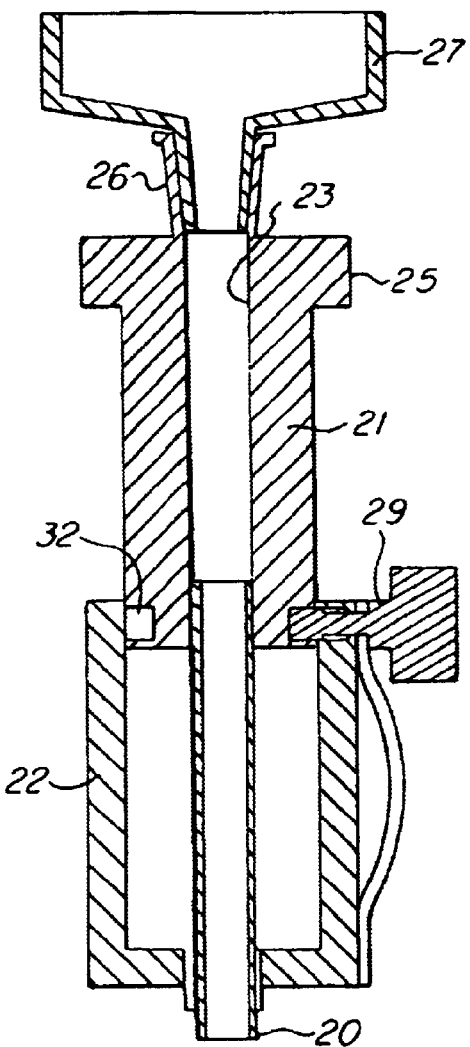
FIGS. 5a and 5b show the arrangement by which the further needles of FIGS. 1 to 3 may be secured to a drug supply and advanced and retracted.

Referring to the drawings, there is shown a hypodermic needle 10 according to the invention. Needle 10 includes a first, hollow, outer needle 11 that is open at its lower end and terminates in a chamfer 12 that defines a sharp point 13 for puncturing of human, animal or plant tissue for the purpose of injection of a substance. The first, hollow needle 11 is typically between 1 and 3 millimeters in diameter and is manufactured eg from surgical steel.

First needle 11 encircles a plurality (4 in the embodiments shown) of smaller, further needles 15 to 18.

In the embodiments shown the further needles 15 to 18 are arranged in a square pattern within the circular interior of first needle 11.

The needles 15 to 18 are retractable and advanceable relative to first needle 11 by means of a mechanism (described below) from a retracted position to the extended position shown in FIGS. 1a and 2.

In their retracted positions (FIG. 3) none of the needles 15 to 18 protrude beyond the chamfer 12 of first hollow needle 11.

When advanced, the needles 15 to 18 protrude longitudinally beyond the end of chamfer 12 and in doing so are each curved through approximately 90° as shown in FIGS. 1a to 2 so that the free ends of the needles 15 to 18 fan out as illustrated. In the preferred embodiment, the needles fan at approximately 90° to one another viewed in plan. However, other angular spacings of the further needles 15 to 18 may be used instead. For example, the needles may all fan out towards the same side of a diagonal of the square pattern shown, in desired.

These effects are achieved through use of an SMA for the manufacture of the needles 15 to 18. The preferred form of alloy is a NiTi allow comprising preferably 56% Ni and 44% Ti (and, optionally, small quantities of other metals such as copper and/or chromium) but other alloys could be used instead. The precise alloy formulation can be selected as desired. Once programmed, the SMA is capable of transforming from a substantially straight alignment (when the needles 15 to 18 are fully retracted within needle 11) to the curved configuration shown in FIGS. 1a and 2.

The needles 15 and 17 are in the embodiments shown shorter than the needles 16 and 18. Thus, the distribution of the substance to the injected occurs at a plurality of locations spaced from one another in the radial and axial directions relative to the needle 11.

Each needle 15 and 18 includes a chamfer 15' to 18' at its free, open end thereby permitting the needles 15 and 18 to penetrate the tissue through which they are advanced.

The attachment of the needles 15 and 18 to a supply of injectable substance, and the advancement and retraction mechanism for the needles 15 to 18, will now be described with reference to FIGS. 4 and 5.

As shown in FIG. 4a, the ends of the further needles 15 and 18 remote from the chamfers extend into an elongate, hollow, substantially straight tube 20. The upper ends of the further needles 15 to 18 are open. Each further needle is sealingly secured in the open end of tube 20 eg. by means of soldering, so that any fluid flowing along tube 20 towards the further needles 15 to 18 passes into the hollow interiors of the further needles 15 and 18.

Tube 20 is slidably received within needle 11. Thus advancement of tube 20 towards the chamfer 12 of needle 11 causes advancement of the further needles 15 to 18 towards their extended (unstressed) configuration shown eg. in FIGS. 1a and 2. Movement of tube 20 away from chamfer 12 of needle 11 causes retraction of the further needles 15 to 18 to the stressed configuration shown in FIG. 3, in which the further needles lie substantially parallel to needle 11.

Needle 11 and tube 20 within it may be of any length suitable for the purpose to which the hypodermic needle 10 is to be put.

The end of tube 20 remote from the further needles 15 to 18 is sealingly secured in a hollow actuator block 21 that is slidably received in a hollow housing 22.

Actuator block 21 has formed therein an axial, through going bore 23 that is in fluid communication with the hollow interior of tube 20.

The end of actuator block 21 remote from tube 20 includes eg. a knurled finger ring 25 by means of which tube 20 may be moved axially within needle 11, thereby permitting selective advancement and retraction of the further needles 15 to 18.

In practice the actuator block 21 and housing 22 are hollow, cylindrical members.

The end of bore 23 remote from tube 20 terminates in a connector 26 of a per se known kind for sealingly receiving the nozzle of a hypodermic syringe shown schematically at 27.

Housing 22 includes a detent in the form of pin 29 that is mounted for sliding motion in a bore passing through the side wall of housing 22 in a direction transverse to the longitudinal axis of the housing.

Pin 29 has at its free end a further knob or finger ring 30 by means of which it may be advanced and retracted through the transverse bore.

A leaf spring 31 secured between pin 29 and a location on the surface of housing 22 remote from pin 29 serves resiliently to bias pin 29 against withdrawal outwards from the transverse bore.

Actuator block 21 includes formed therein adjacent tube 20 an axial groove 32 dimensioned to receive the end of pin 29 when actuator block 21 is withdrawn to the position shown in FIG. 5a. In this configuration, pin 29 serves to lock the actuator block 21 in its retracted or withdrawn position, thereby in turn locking the further needles 15 to 18 at the opposite end of the hypodermic needle 10 in the position shown in FIG. 3 (ie. the stressed condition of the further needles 15 to 18).

Figure 5B:
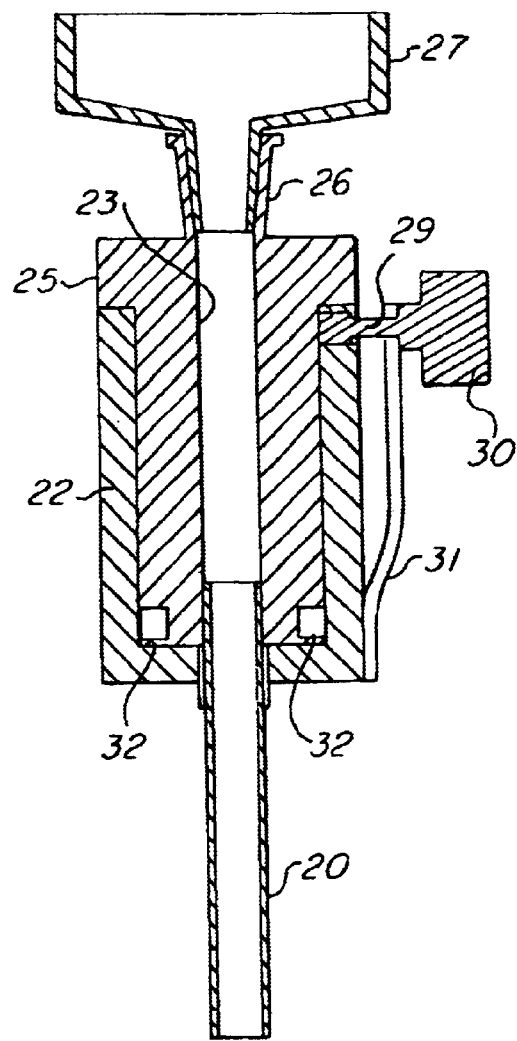

On manual withdrawal of pin 29 from the transverse aperture, actuator block 21 may be pushed home within housing 22, as shown in FIG. 5b, thereby resulting in advancement of the further needles 15 to 18 from the open end of needle 11 (as shown in FIGS. 1, 2 and 4).

As an alternative to the arrangement shown in FIG. 4a, instead of sealingly securing the further needles 15 to 18 in the open end of tube 20, the further needles could extend continuously along the length of tube 20 to emerge at the opposite end thereof. This would in turn permit (through use of suitable adaptors) attachment of individual hypodermic syringes to the respective further needles 15 to 18. Such an arrangement may have some advantages in the pumping of fluids via the further needles 15 to 18, and of course allows the possibility of supplying differing fluids through the respective further needles 15 to 18.

In this alternative embodiment, the tube 20 need not be movable relative to the needle 11. Indeed, if the needle 11 is capable of supporting the further needles 15 to 18 adequately, the tube 20 could be dispensed with.

The needles 15 to 18 would of course be slidable relative either to the tube 20 (if present) or the interior of needle 11, if tube 20 is not present.

The method of operation of the needle 10 of the invention is as follows:

The needle 10 is connected via connector 26 to a source (eg. hypodermic syringe 27) of injectable substance such as eg. alcohol for treatment of liver cancer tumours. The needles 15 to 18 are at this time in their retracted position and hence contained fully within the circular interior of hollow needle 11. The point 13 of the free end of hollow needle 11 is then used to puncture the tissue into which the substance is to be injected. Throughout this part of the operation the further, circular, hollow needles 15 to 18 remain retracted full within needle 11.

Once the free end of needle 13 has penetrated the tissue to the correct depth, the needles 15 to 18 are advanced using the mechanism described hereinabove. This causes the fanning of the needles 15 to 18 as shown in FIGS. 1a and 2, with the chamfers 15' to 18' permitting the free, open ends of the needles 15 to 18 to penetrate the tissue in the volume surrounding needle 11.

Thereafter, the supply of injectable substance is pumped to cause emergence thereof from the free ends of the needles 15 to 18.

Similar techniques may be used when injecting eg. fruit and vegetables and non-living animal matter.

The method of programming the superelastic shape memory alloy, following formation of the further needles 15 to 18 in a substantially straight form, includes heating each said further needle 15 to 18 to a temperature in the range 480° C.–520° C.; supporting the needle on a curved former so that it is forced to adopt the desired curvature for its unstressed condition; and maintaining the temperature of the needle in the aforesaid range, for a time of eg. 8 to 12 minutes. This causes realignment of the cold rolled crystal structure of the further needle in a per se known manner. The result is a needle that substantially adopts the curvature of the former after removal therefrom and cooling.

Although the invention has been described in relation to four smaller needles contained within a single large needle, other arrangements are possible. For example, a greater or smaller number of the smaller needles may be used as desired. Particularly preferred embodiments may include one or three of the further needles. Also, the curvature of the smaller needles may be adjusted by suitable programming of the shape memory alloy, in order to produce desired fanning effects. The lengths of the smaller needles may also be adjusted according to the specific treatment requirement.

The apparatus and method described herein may be modified, within the scope of the invention, to perform alternative functions. For example, the apparatus can be constructed as a multiple point biopsy device, in which the chamfered tips of the further needles are replaced by per se known biopsy heads, operable in a per se known manner remotely from the injection site.

Another possibility is for the further needles to distribute light to a variety of points for diagnostic or therapeutic (eg. photodynamic therapy) purposes. For example, the or each further needle may contain an endoscope device the objective lens of which emerges at the open end of the associated, further needle. The or each further needle could contain an optical fibre or could act as a light guide to convey light to and/or from the further needle free ends.

The or each further needle may include a fluid-tight chamber be means of which a radioactive material may be removably distributed outwardly from the injection site without causing permanent contamination to tissue. The preferred embodiment of the apparatus may be used for injection of radioactive material, if necessary after modification to provide adequate shielding. Yet a further possibility is for the or each further needle to act as a distributed electrode following energisation to a preferred voltage. In this embodiment it may be desirable to insulate the further needles from one another.

What is claimed is:

1. A hypodermic needle comprising a first, hollow needle having a sharp point adapted to puncture tissue and create a wound therein for facilitating advancement of the first needle, and having movably secured therein a plurality of further, hollow needles, each said further needle and the first needle being movable relative to one another between a stressed position of said each further needle, in which each said further needle is substantially parallel to the first needle, and an unstressed position of said each further needle, in which the free end of each said further needle lies beyond at least one of the axial and radial termini of the first needle, wherein the interior of said each further needle communicates with the interior of a hollow, elongate tube movably lying within the first needle, the end of the hollow tube remote from the terminus of the first needle engaging a moveable actuator member for advancing and retracting said each further needle relative to the first needle, and wherein the interior of the hollow tube communicates with an adaptor for receiving the nozzle of a hypodermic syringe.

2. The hypodermic needle according to claim 1 wherein each said further needle includes a circular arc when the further needle is in the unstressed position.

3. The hypodermic needle according to claim 1 wherein each said further needle includes an arc in the range 60°–110° when the further needle is in the unstressed position.

4. The hypodermic needle according to claim 1 wherein each said each further needle includes a straight portion when the further needle is in the unstressed position.

5. The hypodermic needle according to claim 1 wherein each said further needle is formed at least partially from a superelastic shape memory alloy.

6. The hypodermic needle according to claim 5 wherein the superelastic shape memory alloy is a heat treated alloy comprising approximately 56% Ni and 44% Ti.

7. The hypodermic needle according to claim 6, wherein the alloy is heat treated at approximately 500° C. for about 10 minutes whilst secured on a former.

8. The hypodermic needle according to claim 1 wherein said at least one further needle comprises a plurality of further needles, and at least one of said further needles is longer than at least one other of said further needles.

9. The hypodermic needle according to claim 8 wherein the free end of each said longer, further needle is spaced axially and radially from the free end of each said other further needle when the longer and other further needles are in the unstressed position.

10. The hypodermic needle according to claim 1 including a releasable detent for securing the hollow tube in a position corresponding to retraction of said each further needle.

11. A hypodermic needle comprising a first, hollow needle having a sharp point adapted to puncture tissue and create a wound therein for facilitating advancement of the first needle, and a plurality of further, hollow needles lying within the first needle when the further needle is in a stressed position and protruding from the first needle when the further needle is in an unstressed position, wherein the interior of said each further needle communicates with the interior of a hollow, elongate tube movably lying within the first needle, the end of the hollow tube remote from the terminus of the first needle engaging a moveable actuator member for advancing and retracting said each further needle relative to the first needle, and wherein the interior of the hollow tube communicates with an adaptor for receiving the nozzle of a hypodermic syringe.

12. The hypodermic needle comprising a first, hollow needle having a sharp point adapted to puncture tissue and create a wound therein for facilitating advancement of the first needle, and a plurality of further, hollow needles secured therein, wherein each said further needle is generally straight when the further needle is in a stressed position and curved when the further needle is in an unstressed position, thereby permitting the free end of the further needle to project beyond the radial terminus of the first needle when the further needle is in the unstressed position, wherein the interior of said each further needle communicates with the interior of a hollow, elongate tube movably lying within the first needle, the end of the hollow tube remote from the terminus of the first needle engaging a moveable actuator member for advancing and retracting said each further needle relative to the first needle, and wherein the interior of the hollow tube communicates with an adaptor for receiving the nozzle of a hypodermic syringe.

* * * * *